United States Patent [19]

Hillman et al.

[11] Patent Number: 5,863,735
[45] Date of Patent: Jan. 26, 1999

[54] HUMAN TRANSMEMBRANE 4 SUPERFAMILY PROTEIN

[75] Inventors: Jennifer L. Hillman, Mountain View; Surya K. Goli, Sunnyvale, both of Calif.

[73] Assignee: Incyte Pharmaceuticals, Inc., Palo Alto, Calif.

[21] Appl. No.: 807,044

[22] Filed: Feb. 24, 1997

[51] Int. Cl.[6] .............................. C12Q 1/68; C07H 21/04
[52] U.S. Cl. .......................... 435/6; 435/325; 536/23.1; 536/24.31
[58] Field of Search ............................ 536/23.1, 24.31; 435/6, 325

[56] References Cited

PUBLICATIONS

Hillier, L., et al., "The WashU–Merck EST Project," *EMBL Sequence Data Library,* XP002066878, Accession No. AA100695, 30 Oct. 1996.
Tachibana, I., et al., "NAG–2, A Novel Transmembrane–4 Superfamily (TM4SF) Protein That Complexes with Integrins and Other TM4SF Proteins," *The Journal of Biological Chemistry,* vol. 272, No. 46, pp. 29181–29189, XP002066880, Nov. 14, 1997.
Tachibana, I., et al., "NAG–2, A Novel Transmembrane–4 Superfamily (TM4SF) Protein That Complexes with Integrins and Other TM4SF Proteins," *EMBL Sequence Data Library,* XP002066881, Accession No. AF022813, Heidelberg, Germany, Nov. 18, 1997.
Singer, S. J., "The Structure and Insertion of Integral Proteins in Membranes" *Annu. Rev. Cell Biol.* 6:247–296 (1990).
Wright, M.D. and Tomlinson, M.G., "The ins and outs of the transmembrane 4 superfamily" *Immunology Today* 15(12):588–594.
Fitter, S. et al., "Molecular Cloning of cDNA Encoding a Novel Platelet–Endothelial Cell Tetra–Span Antigen, PETA–3" *Blood* 86(4) : 1348–1355 (1995).
Boucheix, C. et al., "Molecular cloning of the CD9 antigen. A new family of cell surface proteins" *J Biol Chem* 266(1):117–122 (1991).
Wright, M.D. et al., "Gene structure, chromosomal localization, and protein sequence of mouse CD53 (Cd53): evidence that the transmembrane 4 superfamily arose by gene duplication" *Int. Immunol.* 5(2):209–216 (1993).
Classon, B.J. et al., "The primary structure of the human leukocyte antigen CD37, a species homologue of the rat MRC OX–44 antigen" *J Exp Med* 169(4):1497–1502 (1989).
Classon, B.J. et al., "The primary structure of the human leukocyte antigen CD37, a species homologue of the rat MRC OX–44 antigen" *J Exp Med* 172(3):1007 (1990) [correction to the article].
Hotta, H. et al., "Molecular Cloning and Characterization of an Antigen Asociated with Early Stages of Melanoma Tumor Progression" *Cancer Research* 48:2955–2962 (1988).

Gaugitsch, H.W. et al., "A new superfamily of lymphoid and melanoma cell proteins with extensive homology to *Schistosoma mansomi* antigen Sm23" *Eur J Immunol* 21(2):377–383 (1991).
Oren, R. et al., "TAPA–1, the Target of an Antiproliferative Antibody Defines a New Family of Transmembrane Proteins" *Mol. Cell. Biol.* 10(8): 4007–4015 (1990).
Szala, S. et al., "Molecular cloning of cDNA for the human tumor–associated antigen CO–029 and identification of related transmembrane antigens" *Proc Natl Acad Sci USA* 87(17):6833–6837.
Kallin, B. et al., "Cloning of a Growth Arrest–Specific and Transforming Growth Factor β–Regulated Gene, TI 1, from an Epithelial Cell Line" *Mol Cell Biol* 11(10):5338–5345 (1991).
Miyake, M. et al., "Identification of the Motility–related Protein (MRP–1), Recognized by Monoclonal Antibody M31–15, Which Inhibits Cell Motility" *J. Exp. Med.* 174:1347–1354 (1991).
Marken, J.S. et al., "Cloning and expression of the tumor–associated antigen L6" *Proc. Natl. Acad. Sci. USA* 89(8):3503–3507 (1992).
Travis, G.H. et al., "The human retinal degeneration slow (RDS) gene: chromosome assignment and structure of the mRNA" *Genomics* 10(3):733–739 1991.
Jankowski, S.A. et al., "SAS a gene amplified in human sarcomas, encodes a new member of the transmembrane 4 superfamily of proteins" *Oncogene* 9:1205–1211 (1994).
Wright, M.D. et al., "An immunogenic $M_r$ 23,000 integral membrane protein of *Schistosom mansoni* worms that closely remembles a human tumor–associated antigen" *J Immunol* 144(8):3195–3200 (1990).
Miyake, M. and Hakomori, S.I., "A Specific Cell Surface Glycoconjugate Controlling Cell Motility: Evidence by Functional Monoclonal Antibodies That Inhibit Cell Motility and Tumor Cell Metastasis" *Biochemistry* 30(13):3328–3334 (1991).

(List continued on next page.)

*Primary Examiner*—Toni R. Scheiner
*Attorney, Agent, or Firm*—Incyte Pharmaceuticals. Inc.; Lucy J. Billings; Leanne C. Price

[57] ABSTRACT

The present invention provides a novel human integral membrane (TMP-1) and polynucleotides which identify and encode TMP-1. The invention also provides genetically engineered expression vectors and host cells comprising the nucleic acid sequences encoding TMP-1 and a method for producing TMP-1. The invention also provides for agonists, antibodies, or antagonists specifically binding TMP-1, and their use, in the prevention and treatment of diseases associated with expression of TMP-1. Additionally, the invention provides for the use of antisense molecules to polynucleotides encoding TMP-1 for the treatment of diseases associated with the expression of TMP-1. The invention also provides diagnostic assays which utilize the polynucleotide, or fragments or the complement thereof, and antibodies specifically binding TMP-1.

7 Claims, 5 Drawing Sheets

OTHER PUBLICATIONS

Ikeyama, S. et al., "Suppression of Cell Motility and Metastasis by Transfection with Human Motility–related Protein (MRP–1/CD9) DNA" *J. Exp. Med.* 177:1231–1237 (1993).

Amiot, M., "Identification and and Analysis of cDNa Clones Encoding CD53: A Pan–Leukocyte Antigen Related to Membrane Transport Proteins" *J. Immunol.* 145:4322–4325 (1990) (GI 180141).

Bell, G.M. et al., "The OX–44 molecule couples to signaling pathways and is associated with CD2 on rat T lymphocytes and a natural killer cell line" *J. Exp. Med.* 175(2):527–536 (1992).

Angelisova, P. et al., "Association of four antigens of the tetraspans family (CD37, CD53, TAPA–1, R2/C33) with MHC class II glycoproteins" *Immunogenetics* 39(4):249–256 (1994).

Olweus, J. et al., "CD53, a protein with four membrane–spanning domains, mediates signal transduction in human monocytes and B cells" *J Immunol* 151(2):707–716 (1993).

Hart, I.R., "The selection and characterization of an invasive variant of the B16 melanoma" *Am J Pathol* 97(3):587–600 (1979).

Wash U–Merck EST Project; Database: Genbank; Subsection EST; Accession No: N40364, 22 Jan. 1996.

Wash U–Merck EST; Project; Database: Genbank; Subsection: EST; Accession No: H08962, 23 Jun. 1995.

WashU–Merck EST Project; Database: Genbank; Subsection: EST; Accession No: N34614, 16 Jan. 1996.

```
                9              18             27             36             45             54
5' TCC TGC TCT GGG CAG AAG GGC AGG ACA GGG GCC CTG AGT AAC GGT GGC CTG GGG 63             72             81             90             99            108
   TCA GAG CCA GGT TCA GCT GCG AGG CTG CTG GTG GCT GTG GAG AGC TTG GGG CTT 117            126            135            144            153            162
   CCT TGG TCG CAC CCA CCA CCT GCC TGC CCA CTG GTC AGC CTT CAG GGA CCC TGA 171            180            189            198            207            216
   GCA CCG CCT GGT CTC TTT CCT GTG GCC AGC CCA GAA CTG AAG CGC TGC GGC ATG
                                                                            M 225            234            243            252            261            270
   GCG CGC GCC TGC CTC CAG GCC GTC AAG TAC CTC ATG TTC GCC TTC AAC CTG CTN
    A   R   A   C   L   Q   A   V   K   Y   L   M   F   A   F   N   L   L 279            288            297            306            315            324
   TTC TGG CTG GGA GGC TGT GGC GTG CTG GGT GTC GGC ATC TGG CTG GCC GCC ACA
    F   W   L   G   G   C   G   V   L   G   V   G   I   W   L   A   A   T 333            342            351            360            369            378
   CAG GGG AGC TTC GCC ACG STG TCC TCT TCC TTC CCG TCC CTG TCG GCT GCC AAC
    Q   G   S   F   A   T   X   S   S   S   F   P   S   L   S   A   A   N 387            396            405            414            423            432
   CTG CTC ATC ATC ACC GGC GCC TTT GTC ATG GCC ATC GGC TTC GTG GGC TGC CTG
    L   L   I   I   T   G   A   F   V   M   A   I   G   F   V   G   C   L 441            450            459            468            477            486
   GGT GCC ATC AAG GAG AAC AAG TGC CTC CTG CTC ACT TTC TTC CTG CTG CTG CTG
    G   A   I   K   E   N   K   C   L   L   L   T   F   F   L   L   L   L 495            504            513            522            531            540
   CTG GTG TTC CTG CTG GAG GCC ACC ATC GCC ATC CTC TTC TTC GCC TAC ACG GAC
    L   V   F   L   L   E   A   T   I   A   I   L   F   F   A   Y   T   D 549            558            567            576            585            594
   AAG ATT GAC AGG TAT GCC CAG CAA GAC CTG AAG AAA GGC TTG CAC CTG TAC GGC
    K   I   D   R   Y   A   Q   Q   D   L   K   K   G   L   H   L   Y   G 603            612            621            630            639            648
   ACG CAG GGC AAC GTG GGC CTC ACC AAC GCC TGG AGC ATC ATC CAG ACC GAC KTC
    T   Q   G   N   V   G   L   T   N   A   W   S   I   I   Q   T   D   X 657            666            675            684            693            702
   CGA GGC GTG GGC AGG TGG GCG GGG TCG GCG GGT GCC CCC TCC CCT NCT GCC TCA
    R   G   V   G   R   W   A   G   S   A   G   A   P   S   P   X   A   S 711            720            729            738            747            756
   GCC CGA CCT GAG CTT GCC CCC CAG TTC CGC TGC TGT GGC GTC TCC AAC TAC ACT
    A   R   P   E   L   A   P   Q   F   R   C   C   G   V   S   N   Y   T
```

FIGURE 1A

```
        765           774           783           792           801           810
GAC TGG TTC GAG GTG TAC AAC GCC ACG CGG GTA CCT GAC TCC TGC TGC TTG GAG
 D   W   F   E   V   Y   N   A   T   R   V   P   D   S   C   C   L   E 819           828           837           846           855           864
TTC AGT GAG AGC TGT GGG CTG CAC GCC CCC GGC ACC TGG TGG AAG GCG CCG TGC
 F   S   E   S   C   G   L   H   A   P   G   T   W   W   K   A   P   C 873           882           891           900           909           918
TAC GAG ACG GTG AAG GTG TGG CTT CAG GAG AAC CTG CTG GCT GTG GGC ATC TTT
 Y   E   T   V   K   V   W   L   Q   E   N   L   L   A   V   G   I   F 927           936           945           954           963           972
GGG CTG TGC ACG GCG CTG GTG CAG ATC CTG GGC CTG ACC TTC GCC ATG ACC ATG
 G   L   C   T   A   L   V   Q   I   L   G   L   T   F   A   M   T   M 981           990           999           1008          1017          1026
TAC TGC CAA GTG GTC AAG GCA GAC ACC TAC TGC GCG TAG GCC GCC CAC CGC CCG
 Y   C   Q   V   V   K   A   D   T   Y   C   A 1035          1044          1053          1062          1071          1080
CTT CTC TGC CAA AAG GAC GCC CAC GGG GAG ATG GCC GCA CCC ACA GCT GCC TTT 1089          1098          1107          1116          1125          1134
CCC ACC ACC AGC CTC GGT GCT CTG CCC CAT GCT GGN ANG AGG GAG GGA GGG ACA

1143
GGT GCC TGG AGC CCC CG 3'
```

FIGURE 1B

```
  1 MARACLQAVKYLMFAFNLLFWLGGCGVLGVGIWLAATQGS           663655
  1 MGMSSLKLLKYVLFFFNLLFWICGCCILGFGIYLL-IHNN           GI 180141

41 FATXSSSFPSLSAANLLIITGAFVMAIGFVGCLGAIKENK           663655
 40 FGVLFHNLPSLTLGNVFVIVGSIHMVVAFLGCMGSIKENK           GI 180141

81 CLLLTFFLLLLLVFLLEATIAILFFAYTDKIDRYAQQDLK           663655
 80 CLLMSFFILLLIILLAEVTLAILLFVYEQKLNEYVAKGLT           GI 180141

121 KGLHLYGTQGNVGLTNAWSIIQTDXRGVGRWAGSAGAPSP           663655
120 DSIHRY------------HSDNSTKAAWDSIQS-------           GI 180141

161 XASARPELAPQFRCCGVSNYTDWFEEVYNATRVPDSC-CLE           663655
141 F-----------LQCCGINGTSDW----TSGPPASCPSDR           GI 180141

201 FSESCGLHAPGTWWKAPCYETVKVWLQENLLAVGIFGLCT           663655
162 KVEGC-----------YAKARLWFHSNFLYIGIITICV              GI 180141

241 ALVQILGLTFAMTMYCQVVKA-DTYCA                         663655
194 CVIEVLGMSFALTLNCQIDKTSQTIGL                         GI 180141
```

FIGURE 2

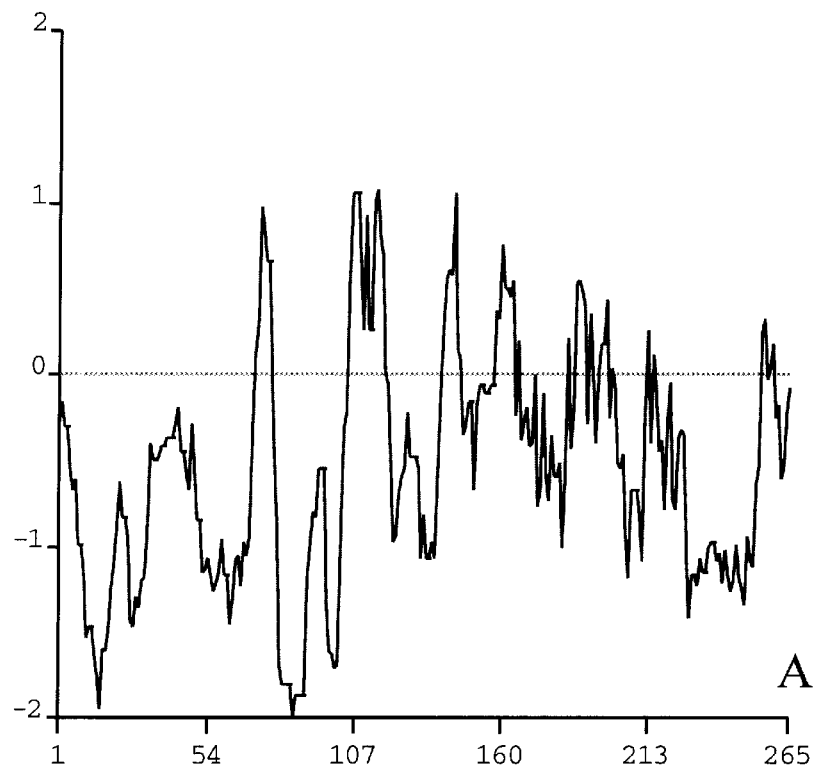
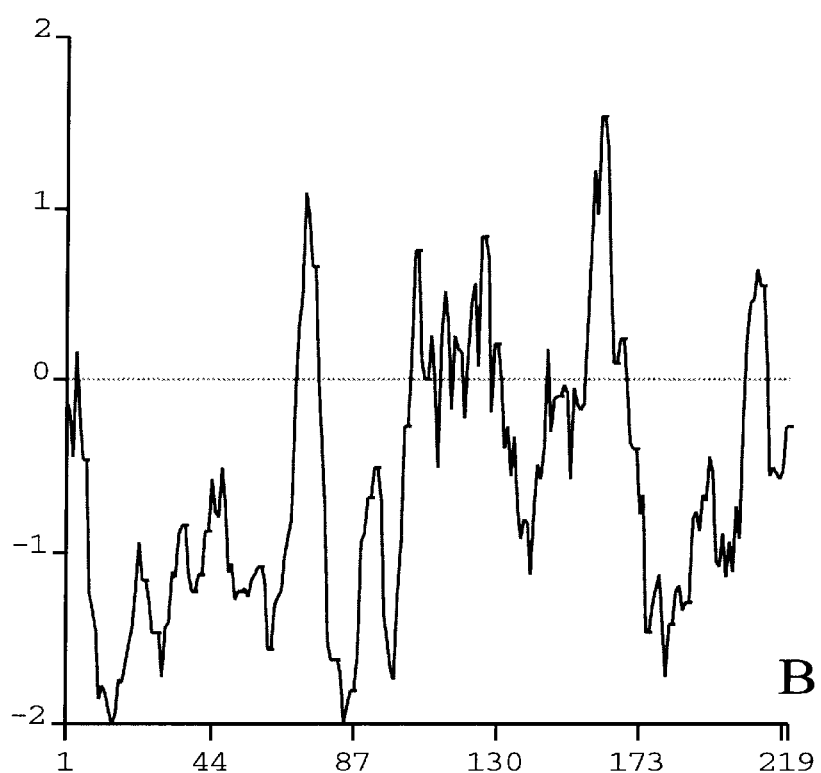
FIGURE 3

| Library | Lib Description | Abun | Pct Abun |
|---|---|---|---|
| UTRSNOT06 | uterus, myometrium, 50 F | 3 | 0.0847 |
| LUNGNOT14 | lung, 47 M | 3 | 0.0778 |
| DUODNOT01 | small intestine, duodenum, 41 F | 2 | 0.0575 |
| PROSTUT12 | prostate tumor, 65 M, match to PROSNOT20 | 2 | 0.0559 |
| CONNTUT01 | skull tumor, chondroid chordoma, 30 F | 2 | 0.0541 |
| BLADTUT05 | bladder tumor, 66 M, match to BLADNOT06 | 2 | 0.0536 |
| BLADNOT05 | bladder, 60 M, match to BLADTUT04 | 2 | 0.0528 |
| BRAITUT13 | brain tumor, meningioma, 68 M | 2 | 0.0524 |
| BRSTTUT08 | breast tumor, 45 F, match to BRSTNOT09 | 2 | 0.0507 |
| BRAINOM02 | brain, 55 M, NORM, WM | 1 | 0.0454 |
| BRSTTUT02 | breast tumor, 54 F, match to BRSTNOT03 | 3 | 0.0419 |
| MUSCNOT02 | muscle, psoas, 12 M | 1 | 0.0386 |
| LUNGNOT20 | lung, 61 M | 1 | 0.0309 |
| LUNGNOT18 | lung, 66 F | 1 | 0.0298 |
| FIBRSEM01 | fibroblasts, senescent, NORM, WM | 1 | 0.0289 |
| PANCNOT07 | pancreas, fetal M | 1 | 0.0287 |
| SYNORAT05 | synovium, knee, rheumatoid, 62 F | 1 | 0.0286 |
| LUNGNOT12 | lung, 78 M | 1 | 0.0278 |
| LUNGNOT15 | lung, 69 M, match to LUNGTUT03 | 1 | 0.0276 |
| PROSNOT19 | prostate, 59 M | 1 | 0.0272 |
| BLADNOT03 | bladder, 80 F, match to BLADTUT02 | 1 | 0.0271 |
| KIDNTUT01 | kidney tumor, Wilms, 8m F | 1 | 0.0267 |
| COLNNOT23 | colon, ulcerative colitis, 16 M | 1 | 0.0264 |
| BRAITUT07 | brain tumor, left frontal, 32 M | 1 | 0.0259 |
| HEARFET01 | heart, fetal M | 1 | 0.0254 |
| SPLNFET02 | spleen, fetal M | 2 | 0.0252 |
| CARDFEM01 | heart, fetal, NORM, WM | 3 | 0.0249 |
| GBLATUT01 | gall bladder tumor, 78 F | 1 | 0.0241 |
| PROSNOT15 | prostate, 66 M, match to PROSTUT10 | 1 | 0.0241 |
| ENDCNOT03 | endothelial cells, neonatal M | 1 | 0.0210 |
| SCORNOT01 | spinal cord, 71 M | 1 | 0.0201 |
| CRBLNOT01 | brain, cerebellum, 69 M | 1 | 0.0195 |
| BRSTNOT04 | breast, 62 F | 2 | 0.0192 |
| MELANOM01 | melanocytes, M, NORM, WM | 2 | 0.0192 |
| HNT3AZT01 | hNT2 cell line, teratocarcinoma, treated AZ | 1 | 0.0191 |
| BRSTTUT01 | breast tumor, 55 F, match to BRSTNOT02 | 2 | 0.0189 |
| LUNGTUT02 | lung tumor, metastasis, 79 M | 1 | 0.0189 |
| HNT2RAT01 | hNT2 cell line, teratocarcinoma, treated RA | 1 | 0.0188 |
| BRAINOT03 | brain, 26 M | 1 | 0.0185 |
| LUNGNOT04 | lung, 2 M | 1 | 0.0183 |
| UTRSNOT02 | uterus, 34 F | 2 | 0.0155 |
| COLNNOT11 | colon, 60 M | 1 | 0.0149 |
| NGANNOT01 | ganglioneuroma, 9 M | 2 | 0.0146 |
| PROSTUT05 | prostate tumor, 69 M, match to PROSNOT07 | 1 | 0.0145 |
| THYRNOT03 | thyroid tumor, adenoma, 28 F | 1 | 0.0138 |
| BRAINOM01 | brain, infant F, NORM, WM | 3 | 0.0134 |
| TESTTUT02 | testicular tumor, 31 M | 1 | 0.0134 |
| BRAITUT01 | brain tumor, oligoastrocytoma, 50 F | 1 | 0.0134 |
| ENDANOT01 | endothelial cells, aorta, M | 1 | 0.0128 |
| SPLNNOT04 | spleen, 2 M | 1 | 0.0128 |
| PROSTUT04 | prostate tumor, 57 M, match to PROSNOT06 | 1 | 0.0117 |
| PROSNOT06 | prostate, 57 M, match to PROSTUT04 | 1 | 0.0114 |
| BRSTNOT02 | breast, 55 F, match to BRSTTUT01 | 1 | 0.0111 |
| LUNGAST01 | lung, asthma, 17 M | 1 | 0.0094 |
| BRAINOT09 | brain, fetal M | 1 | 0.0093 |
| BRAITUT02 | brain tumor, metastasis, 58 M | 1 | 0.0075 |

FIGURE 4

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 265 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: SCORNOT01
        ( B ) CLONE: 663655

( x i ) SEQUENCE DESCRIPTION: SEQ ID NO:1:

```
Met  Ala  Arg  Ala  Cys  Leu  Gln  Ala  Val  Lys  Tyr  Leu  Met  Phe  Ala  Phe
 1              5                        10                       15

Asn  Leu  Leu  Phe  Trp  Leu  Gly  Gly  Cys  Gly  Val  Leu  Gly  Val  Gly  Ile
              20                        25                       30

Trp  Leu  Ala  Ala  Thr  Gln  Gly  Ser  Phe  Ala  Thr  Xaa  Ser  Ser  Ser  Phe
              35                        40                       45

Pro  Ser  Leu  Ser  Ala  Ala  Asn  Leu  Leu  Ile  Ile  Thr  Gly  Ala  Phe  Val
     50                        55                        60

Met  Ala  Ile  Gly  Phe  Val  Gly  Cys  Leu  Gly  Ala  Ile  Lys  Glu  Asn  Lys
65                        70                        75                       80

Cys  Leu  Leu  Leu  Thr  Phe  Phe  Leu  Leu  Leu  Leu  Leu  Val  Phe  Leu  Leu
                    85                        90                       95

Glu  Ala  Thr  Ile  Ala  Ile  Leu  Phe  Phe  Ala  Tyr  Thr  Asp  Lys  Ile  Asp
               100                       105                      110

Arg  Tyr  Ala  Gln  Gln  Asp  Leu  Lys  Lys  Gly  Leu  His  Leu  Tyr  Gly  Thr
          115                      120                       125

Gln  Gly  Asn  Val  Gly  Leu  Thr  Asn  Ala  Trp  Ser  Ile  Ile  Gln  Thr  Asp
     130                      135                            140

Xaa  Arg  Gly  Val  Gly  Arg  Trp  Ala  Gly  Ser  Ala  Gly  Ala  Pro  Ser  Pro
145                           150                      155                 160

Xaa  Ala  Ser  Ala  Arg  Pro  Glu  Leu  Ala  Pro  Gln  Phe  Arg  Cys  Cys  Gly
                    165                      170                       175

Val  Ser  Asn  Tyr  Thr  Asp  Trp  Phe  Glu  Val  Tyr  Asn  Ala  Thr  Arg  Val
               180                      185                       190

Pro  Asp  Ser  Cys  Cys  Leu  Glu  Phe  Ser  Glu  Ser  Cys  Gly  Leu  His  Ala
          195                      200                       205

Pro  Gly  Thr  Trp  Trp  Lys  Ala  Pro  Cys  Tyr  Glu  Thr  Val  Lys  Val  Trp
```

```
         210                       215                       220
Leu Gln Glu Asn Leu Leu Ala Val Gly Ile Phe Gly Leu Cys Thr Ala
225                 230                 235                 240

Leu Val Gln Ile Leu Gly Leu Thr Phe Ala Met Thr Met Tyr Cys Gln
                245                 250                 255

Val Val Lys Ala Asp Thr Tyr Cys Ala
                260             265
```

( 2 ) INFORMATION FOR SEQ ID NO:2:

( i ) SEQUENCE CHARACTERISTICS:
        ( A ) LENGTH: 1151 base pairs
        ( B ) TYPE: nucleic acid
        ( C ) STRANDEDNESS: single
        ( D ) TOPOLOGY: linear ( v i i ) IMMEDIATE SOURCE:
        ( A ) LIBRARY: SCORNOT01
        ( B ) CLONE: 663655

( x i ) SEQUENCE DESCRIPTION: SEQ ID NO:2:

```
TCCTGCTCTG  GGCAGAAGGG  CAGGACAGGG  GCCCTGAGTA  ACGGTGGCCT  GGGGTCAGAG    60

CCAGGTTCAG  CTGCGAGGCT  GCTGGTGGCT  GTGGAGAGCT  TGGGGCTTCC  TTGGTCGCAC   120

CCACCACCTG  CCTGCCCACT  GGTCAGCCTT  CAGGGACCCT  GAGCACCGCC  TGGTCTCTTT   180

CCTGTGGCCA  GCCCAGAACT  GAAGCGCTGC  GGCATGGCGC  GCGCCTGCCT  CCAGGCCGTC   240

AAGTACCTCA  TGTTCGCCTT  CAACCTGCTN  TTCTGGCTGG  GAGGCTGTGG  CGTGCTGGGT   300

GTCGGCATCT  GGCTGGCCGC  CACACAGGGG  AGCTTCGCCA  CGSTGTCCTC  TTCCTTCCCG   360

TCCCTGTCGG  CTGCCAACCT  GCTCATCATC  ACCGGCGCCT  TTGTCATGGC  CATCGGCTTC   420

GTGGGCTGCC  TGGGTGCCAT  CAAGGAGAAC  AAGTGCCTCC  TGCTCACTTT  CTTCCTGCTG   480

CTGCTGCTGG  TGTTCCTGCT  GGAGGCCACC  ATCGCCATCC  TCTTCTTCGC  CTACACGGAC   540

AAGATTGACA  GGTATGCCCA  GCAAGACCTG  AAGAAAGGCT  TGCACCTGTA  CGGCACGCAG   600

GGCAACGTGG  GCCTCACCAA  CGCCTGGAGC  ATCATCCAGA  CCGACKTCCG  AGGCGTGGGC   660

AGGTGGGCGG  GGTCGGCGGG  TGCCCCCTCC  CCTNCTGCCT  CAGCCCGACC  TGAGCTTGCC   720

CCCCAGTTCC  GCTGCTGTGG  CGTCTCCAAC  TACACTGACT  GGTTCGAGGT  GTACAACGCC   780

ACGCGGGTAC  CTGACTCCTG  CTGCTTGGAG  TTCAGTGAGA  GCTGTGGGCT  GCACGCCCCC   840

GGCACCTGGT  GGAAGGCGCC  GTGCTACGAG  ACGGTGAAGG  TGTGGCTTCA  GGAGAACCTG   900

CTGGCTGTGG  GCATCTTTGG  GCTGTGCACG  GCGCTGGTGC  AGATCCTGGG  CCTGACCTTC   960

GCCATGACCA  TGTACTGCCA  AGTGGTCAAG  GCAGACACCT  ACTGCGCGTA  GGCCGCCCAC  1020

CGCCCGCTTC  TCTGCCAAAA  GGACGCCCAC  GGGGAGATGG  CCGCACCCAC  AGCTGCCTTT  1080

CCCACCACCA  GCCTCGGTGC  TCTGCCCCAT  GCTGGNANGA  GGGAGGGAGG  GACAGGTGCC  1140

TGGAGCCCCC  G                                                          1151
```

( 2 ) INFORMATION FOR SEQ ID NO:3:

( i ) SEQUENCE CHARACTERISTICS:
        ( A ) LENGTH: 219 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 180141

( x i ) SEQUENCE DESCRIPTION: SEQ ID NO:3:

| | | | | | | | | | | | | | | |
|---|---|---|---|---|---|---|---|---|---|---|---|---|---|---|
| Met<br>1 | Gly | Met | Ser | Ser<br>5 | Leu | Lys | Leu | Leu | Lys<br>10 | Tyr | Val | Leu | Phe | Phe<br>15 | Phe |
| Asn | Leu | Leu | Phe<br>20 | Trp | Ile | Cys | Gly | Cys<br>25 | Cys | Ile | Leu | Gly | Phe<br>30 | Gly | Ile |
| Tyr | Leu | Leu<br>35 | Ile | His | Asn | Asn | Phe<br>40 | Gly | Val | Leu | Phe | His<br>45 | Asn | Leu | Pro |
| Ser | Leu<br>50 | Thr | Leu | Gly | Asn | Val<br>55 | Phe | Val | Ile | Val | Gly<br>60 | Ser | Ile | Ile | Met |
| Val<br>65 | Val | Ala | Phe | Leu | Gly<br>70 | Cys | Met | Gly | Ser | Ile<br>75 | Lys | Glu | Asn | Lys | Cys<br>80 |
| Leu | Leu | Met | Ser | Phe<br>85 | Phe | Ile | Leu | Leu | Leu<br>90 | Ile | Ile | Leu | Leu | Ala<br>95 | Glu |
| Val | Thr | Leu | Ala<br>100 | Ile | Leu | Leu | Phe | Val<br>105 | Tyr | Glu | Gln | Lys | Leu<br>110 | Asn | Glu |
| Tyr | Val | Ala<br>115 | Lys | Gly | Leu | Thr | Asp<br>120 | Ser | Ile | His | Arg | Tyr<br>125 | His | Ser | Asp |
| Asn | Ser<br>130 | Thr | Lys | Ala | Ala | Trp<br>135 | Asp | Ser | Ile | Gln | Ser<br>140 | Phe | Leu | Gln | Cys |
| Cys<br>145 | Gly | Ile | Asn | Gly | Thr<br>150 | Ser | Asp | Trp | Thr | Ser<br>155 | Gly | Pro | Pro | Ala | Ser<br>160 |
| Cys | Pro | Ser | Asp | Arg<br>165 | Lys | Val | Glu | Gly | Cys<br>170 | Tyr | Ala | Lys | Ala | Arg<br>175 | Leu |
| Trp | Phe | His | Ser<br>180 | Asn | Phe | Leu | Tyr | Ile<br>185 | Gly | Ile | Ile | Thr | Ile<br>190 | Cys | Val |
| Cys | Val | Ile<br>195 | Glu | Val | Leu | Gly | Met<br>200 | Ser | Phe | Ala | Leu | Thr<br>205 | Leu | Asn | Cys |
| Gln | Ile | Asp<br>210 | Lys | Thr | Ser | Gln<br>215 | Thr | Ile | Gly | Leu | | | | | |

( 2 ) INFORMATION FOR SEQ ID NO:4:

( i ) SEQUENCE CHARACTERISTICS:
        ( A ) LENGTH: 1452 base pairs
        ( B ) TYPE: nucleic acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 180140

( x i ) SEQUENCE DESCRIPTION: SEQ ID NO:4:

```
CTCAAGGATA  ATCACTAAAT  TCTGCCGAAA  GGACTGAGGA  ACGGTGCCTG  GAAAAGGGCA     60
AGAATATCAC  GGCATGGGCA  TGAGTAGCTT  GAAACTGCTG  AAGTATGTCC  TGTTTTTCTT    120
CAACTTGCTC  TTTTGGATCT  GTGGCTGCTG  CATTTTGGGC  TTTGGGATCT  ACCTGCTGAT    180
CCACAACAAC  TTCGGAGTGC  TCTTCCATAA  CCTCCCCTCC  CTCACGCTGG  GCAATGTGTT    240
TGTCATCGTG  GGCTCTATTA  TCATGGTAGT  TGCCTTCCTG  GGCTGCATGG  GCTCTATCAA    300
GGAAAACAAG  TGTCTGCTTA  TGTCGTTCTT  CATCCTGCTG  CTGATTATCC  TCCTTGCTGA    360
GGTGACCTTG  GCCATCCTGC  TCTTTGTATA  TGAACAGAAG  CTGAATGAGT  ATGTGGCTAA    420
GGGTCTGACC  GACAGCATCC  ACCGTTACCA  CTCAGACAAT  AGCACCAAGG  CAGCGTGGGA    480
CTCCATCCAG  TCATTTCTGC  AGTGTTGTGG  TATAAATGGC  ACGAGTGATT  GGACCAGTGG    540
CCCACCAGCA  TCTTGCCCCT  CAGATCGAAA  AGTGGAGGGT  TGCTATGCGA  AAGCAAGACT    600
GTGGTTTCAT  TCCAATTTCC  TGTATATCGG  AATCATCACC  ATCTGTGTAT  GTGTGATTGA    660
```

-continued

| | | | | | | |
|---|---|---|---|---|---|---|
| GGTGTTGGGG | ATGTCCTTTG | CACTGACCCT | GAACTGCCAG | ATTGACAAAA | CCAGCCAGAC | 720 |
| CATAGGGCTA | TGATCTGCAG | TAGTTCTGTG | GTGAAGAGAC | TTGTTTCATC | TCCGGAAATG | 780 |
| CAAAACCATT | TATAGCATGA | AGCCCTACAT | GATCACTGCA | GGATGATCCT | CCTCCCATCC | 840 |
| TTTCCCTTTT | TAGGTCCCTG | TCTTATACAA | CCAGAGAAGT | GGGTGTTGGC | CAGGCACATC | 900 |
| CCATCTCAGG | CAGCAAGACA | ATCTTTCACT | CACTGACGGC | AGCAGCCATG | TCTCTCAAAG | 960 |
| TGGTGAAACT | AATATCTGAG | CATCTTTTAG | ACAAGAGAGG | CAAAGACAAA | CTGGATTTAA | 1020 |
| TGGCCCAACA | TCAAAGGGTG | AACCCAGGAT | ATGAATTTTT | GCATCTTCCC | ATTGTCGAAT | 1080 |
| TAGTCTCCAG | CCTCTAAATA | ATGCCCAGTC | TTCTCCCCAA | AGTCAAGCAA | GAGACTAGTT | 1140 |
| GAAGGGAGTT | CTGGGGCCAG | GCTCACTGGA | CCATTGTCAC | AACCCTCTGT | TTCTCTTTGA | 1200 |
| CTAAGTGCCC | TGGCTACAGG | AATTACACAG | TTCTCTTTCT | CCAAAGGGCA | AGATCTCATT | 1260 |
| TCAATTTCTT | TATTAGAGGG | CCTTATTGAT | GTGTTCTAAG | TCTTTCCAGA | AAAAAACTAT | 1320 |
| CCAGTGATTT | ATATCCTGAT | TTCAACCAGT | CACTTAGCTG | ATAATCACAG | TAAGAAGACT | 1380 |
| TCTGGTATTA | TCTCTCTATC | AGATAAGATT | TTGTTAATGT | ACTATTTTAC | TCTTCAATAA | 1440 |
| ATAAAACAGT | TT | | | | | 1452 |

HUMAN TRANSMEMBRANE 4 SUPERFAMILY PROTEIN

FIELD OF THE INVENTION

This invention relates to nucleic acid and amino acid sequences of a novel transmembrane protein, TMP-1, and to the use of these sequences in the diagnosis, prevention, and treatment of disease.

BACKGROUND OF THE INVENTION

Membrane proteins are divided into two groups based upon the ease with which the proteins can be removed from the membrane. Extrinsic or peripheral membrane proteins can be removed using extremes of ionic strength or pH, the use of urea or other disruptors of protein interactions. Intrinsic or integral membrane proteins are released only when the lipid bilayer of the membrane is dissolved by detergent.

The majority of known integral membrane proteins are transmembrane proteins which comprises an extracellular, a transmembrane, and an intracellular domain. Transmembrane proteins are typically embedded into the cell membrane by one or more regions comprising 15 to 25 hydrophobic amino acids which are predicted to adopt an α-helical conformation. Transmembrane proteins are classified as bitopic (or Types I and II) and polytopic (or Types III and IV) [Singer, S. J. (1990) Annu. Rev. Cell Biol. 6:247–96]. Bitopic proteins span the membrane once while polytopic proteins contain multiple membrane-spanning segments. Type III integral membrane proteins have multiple transmembrane stretches of hydrophobic residues. Transmembrane proteins carry out a variety of important cellular functions such as acting as cell-surface receptor proteins which are involved in signal transduction (e.g., growth factor receptors) and transport of ions or metabolites (e.g., ion channels).

Recently a multigene family encoding type III integral membrane proteins, termed the transmembrane 4 superfamily (TM4SF) or tetraspan family, was identified [Wright, M. D. and Tomlinson, M. G. (1994) Immunol. Today 15:588]. The TM4SF family comprises a superfamily of membrane proteins which cross or traverse the cell membrane four times. Members of the TM4SF include a number of platelet and endothelial cell membrane proteins [PETA-3, CD9 (lung adenocarcinoma antigen MRP-1), the platelet and melanoma-associated antigen CD63 (ME491)], leukocyte surface glycoproteins [CD53, CD37, CD63, R2, and the tumor associated antigen TAPA-1 (CD81)], the colonal carcinoma antigen CO-029, mink lung epithelial protein TI-1, the tumor-associated antigen L6, SAS (a gene amplified in human sarcomas), the product of a gene responsible for slow retinal degeneration in mice (the rds gene product), and surface proteins of the schistosome parasites [Fitter, S. et al. (1995) Blood 86:1348; Boucheix et al. (1991) J. Biol. Chem. 266:117; Wright, M. D. et al. (1993), Int. Immunol. 5:209; Classon, B. J. (1989) J. Exp. Med. 169:1497 and (1990) J. Exp. Med. 172:1007; Hotta, J. et al. (1988) Cancer Res. 48:2955; Gaugitsch, T. et al. (1991) Eur. J. Immunol. 21:377; Oren, R. et al. (1990) Mol. Cell. Biol. 10:4007; Szala, S. et al. Proc. Natl. Acad. Sci. USA 87:6833; Kallin, B. et al. (1991) Mol. Cell. Biol. 11:5338; Miyake, M. (1991) J. Exp. Med. 174:1347; Marken, J. S. et al. (1992) Proc. Natl. Acad. Sci. USA 89:3503; Travis, G. H. et al. (1991) Genomics 10:733–739, Jankowski, S. A. (1994) Oncogene 9:1205; and Wright, M. D. et al. (1990) J. Immunol. 144:3195]. The members of the TM4SF show about 25–30% amino acid sequence identity with one another.

The predicted structure of the TM4SF proteins reveals a topology where the N- and C-termini are intracellular and the major hydrophilic domain, located between transmembrane domains 3 and 4, is extracellular. TM4SF members are most conserved in their transmembrane and cytoplasmic domains (the conservation among transmembrane domains being the highest) and most divergent in their two hydrophilic extracellular domains. The high level of conservation seen in the transmembrane and cytoplasmic domains of TM4SF members suggest an effector/signaling function common to all members. The divergence of the extracellular domains suggests these domains provide functions specific to each family member such as ligand binding or protein-protein interaction [Wright, M. D. et al. (1993), supra and Fitter, S. et al., supra].

A number of TM4SF members have been implicated in signal transduction, control of cell adhesion, regulation of cell growth and proliferation (including development and oncogenesis) and motility (including the ability to suppress metastatic potential) and expression of a number of TM4SF members is associated with a variety of tumors (e.g., CD81/TAPA-1,L6, CD9/MRP-1, L6, CD63/ME491, CO-029, SAS, PETA-3). Indeed the expression of several TM4SF members is altered when cells are growing or activated. CD9, CD53 and CD82 are upregulated when lymphocytes are activated. Cell surface expression of CD37 is rapidly lost upon activation of B cells. Other TM4SF members are implicated in cell growth due to their association with tumor cells. CD9 (MRP-1) is a marker for 90% of non-T acute lymphoblastic leukemia cells and 50% of acute myeloid and chronic lymphoid leukemias; CD9 is not expressed on resting B and T lymphocytes. Anti-CD9 antibodies inhibits the motility of a variety of cancer cell lines and inhibits the metastatic potential of the mouse BL6 cell line, a highly metastatic variant of B16 cells [Miyake, M. and Hakomori, S. (1991) Biochem. 30:3328]. Expression of CD9 in transfection experiments correlated with suppression of metastatic potential and cell motility [Ikeyama, S. et al. (1993) J. Exp. Med. 174:1347]. CD63 (ME491) is expressed in early stage melanoma but is downregulated in advanced stages of melanoma; CD63 is not expressed on normal tissue melanocytes. CO-029 is expressed on colon, gastric, pancreatic and rectal carcinomas but not on most normal tissues. The gene encoding SAS is amplified in a subset of human sarcomas.

CD53 is a recently characterized member of the TM4SF [Amiot, M. (1990) J. Immunol. 145:4322 and Wright, M. D. et al. (1993), supra] (CD53 is also known as the rat OX44 antigen). CD53 is a glycoprotein which is expressed on the surface of all nucleated cells of hematopoietic origin and CD53 transcripts are dramatically increased following cell activation. Among the TM4SF members, CD53 is most closely related to CD37 and CD82 (R2), a marker which is upregulated upon activation of B and T cells (Wright, M. D. and Tomlinson, M. G., supra). CD53 is distantly related to a bacterial type III integral membrane protein that transports lactose into cells (*E. coli* lac Y permease) and it has been suggested in view of this homology and the upregulation of CD53 following mitogenic stimulation of lymphocytes that CD53 may be involved in the transport of factors required for cell proliferation [Amiot, M., supra]. CD53, like other members of the TM4SF, has been shown to be a component of transmembrane signaling complexes. CD53 associates with CD2 on T cells and natural killer cells [Bell, G. M. (1992) J. Exp. Med. 175:527] and it is found in a complex containing CD37, TAPA-1, CD82 and MHC class I or II molecules in B cells [Angelisova, P. (1994) Immunogenetics 39:249].

Biochemical data demonstrates that CD53 is coupled to signal transduction pathways. Anti-CD53 antibodies cause calcium fluxes in human B cells, granulocytes and monocytes along with activation of the monocyte oxidative burst [Olweus, J. et al. (1993) J. Immunol. 151:707]. In the rat, anti-CD53 antibodies stimulate an inositol phosphate response, protein phosphorylation and an increase in intracellular free calcium; the anti-rat CD53 antibody 7D2 is mitogenic for splenic T cells [Bell, G. M. et al., supra]. Thus, CD53 is involved in the regulation of cell proliferation and activation.

The discovery of molecules related in the TM4SF multigene family satisfies a need in the art by providing new diagnostic or therapeutic compositions useful in the treatment of disorders associated with alterations in the expression of members of the TM4SF multigene family.

SUMMARY OF THE INVENTION

The present invention features a novel integral membrane protein hereinafter designated TMP-1 and characterized as having similarity to the human CD53 integral membrane protein and other members of the TM4SF.

Accordingly, the invention features a substantially purified polypeptide having the amino acid sequence shown in SEQ ID NO:1 or fragments thereof. Preferred fragments of SEQ ID NO:1 are fragments of about 15 amino acids or greater in length which define fragments unique (i.e., having less than about 25% identity to fragments of another protein) to SEQ ID NO:1 or which retain biological activity or immunological activity (i.e., capable of eliciting anti-TMP-1 antibodies). Fragments of SEQ ID NO:1 which are at least 25 amino acids, at least 50 amino acids, at least 100 amino acids, at least 125 amino acids, at least 200 amino acids and at least 250 amino acids in length are contemplated.

The present invention further provides isolated and substantially purified polynucleotide sequences encoding the polypeptide comprising the amino acid sequence of SEQ ID NO:1 or fragments thereof. In a particular aspect, the polynucleotide is the nucleotide sequence of SEQ ID NO:2 or variants thereof. In another embodiment, the present invention provides polynucleotides comprising fragments of SEQ ID NO:2 having a length greater than 20 nucleotides. The invention further contemplates fragments of this polynucleotide sequence (i.e., SEQ ID NO:2) that are at least 50 nucleotides, at least 100 nucleotides, at least 250 nucleotides, at least 500 nucleotides and at least 1000 nucleotides in length.

In addition, the invention provides polynucleotide sequences which hybridize under stringent conditions to the polynucleotide sequence of SEQ ID NO:2. In another embodiment the present invention provides a composition comprising an isolated and purified polynucleotide sequence encoding TMP-1.

The invention provides polynucleotide sequences comprising the complement of SEQ ID NO:2 or variants thereof; these complementary nucleic acid sequences may comprise the complement of the entire nucleic acid sequence of SEQ ID NO:2 or fragments thereof. In another embodiment the present invention provides a composition comprising an isolated and purified polynucleotide sequence comprising the complement of SEQ ID NO:2 or variants thereof.

The invention additionally features nucleic acid sequences encoding polypeptides, oligonucleotides, peptide nucleic acids (PNA), fragments, portions or antisense molecules thereof, and expression vectors and host cells comprising polynucleotides that encode TMP-1.

In another embodiment the present invention provides an isolated polynucleotide comprising at least a portion of the nucleic acid sequence of SEQ ID NO:2 or variants thereof contained on a recombinant expression vector. In yet another embodiment, the expression vector containing the polynucleotide sequence is contained within a host cell. The invention is not limited by the nature of the host cell employed. For example, the host cell may be an E. coli cell, a yeast cell, an insect cell, a mammalian cell, etc.

The present invention also provides a method for producing a polypeptide comprising the amino acid sequence of SEQ ID NO:1 or fragments thereof, the method comprising the steps of: a) culturing the host cell containing an expression vector containing an isolated polynucleotide encoding at least a fragment of the TMP-1 polypeptide under conditions suitable for the expression of the polypeptide; and b) recovering the polypeptide from the host cell culture.

In another embodiment, the invention provides a pharmaceutical composition comprising a substantially purified human TMP-1 protein having the amino acid sequence of SEQ ID NO:1 in conjunction with a suitable pharmaceutical carrier.

The invention also provides a purified antibody which binds specifically to a polypeptide comprising at least a portion of the amino acid sequence of SEQ ID NO:1.

Still further, the invention provides a purified agonist which specifically binds to and modulates the activity of a polypeptide comprising at least a portion of the amino acid sequence of SEQ ID NO:1. The present invention further provides a pharmaceutical composition comprising a purified agonist which specifically binds to and modulates the activity of a polypeptide comprising at least a portion of the amino acid sequence of SEQ ID NO:1. In another embodiment, the invention provides a purified antagonist which specifically binds to and modulates the activity of a polypeptide comprising at least a portion of the amino acid sequence of SEQ ID NO:1. The present invention further provides a pharmaceutical composition comprising a purified antagonist which specifically binds to and modulates the activity of a polypeptide comprising at least a portion of the amino acid sequence of SEQ ID NO:1.

The invention also provides a method for treating metastatic tumors (including lung and brain metastases) comprising administering to a subject in need of such treatment an effective amount of a pharmaceutical composition comprising a purified agonist which specifically binds to and modulates the activity of a polypeptide comprising at least a portion of the amino acid sequence of SEQ ID NO:1. The treatment of a variety of tumors, including but not limited to tumors of the prostate, breast, bladder, testis, thyroid, kidney, skull and gall bladder, using agonists as well as antagonists of TMP-1 is also contemplated by the present invention.

The invention also provides a method for the detection of polynucleotides encoding human TMP-1 in a biological sample comprising the steps of: a) hybridizing a polynucleotide sequence encoding human TMP-1 (SEQ ID NO:1) to nucleic acid material of a biological sample, thereby forming a hybridization complex; and b) detecting the hybridization complex, wherein the presence of the complex correlates with the presence of a polynucleotide encoding human TMP-1 in the biological sample. In a preferred embodiment, prior to hybridization, the nucleic acid material of the biological sample is amplified by the polymerase chain reaction.

BRIEF DESCRIPTION OF THE FIGURES

Figures 1A and 1B show the amino acid sequence (SEQ ID NO:1) and nucleic acid sequence (SEQ ID NO:2) of TMP-1. The alignment was produced using MACDNASIS PRO software (Hitachi Software Engineering Co., Ltd., San Bruno, Calif.).

FIG. 2 shows the amino acid sequence alignments between TMP-1 (SEQ ID NO:1) and human CD53 (GI 180141; SEQ ID NO:3). The alignment was produced using the multisequence alignment program of DNASTAR software (DNASTAR Inc, Madison Wis.).

FIG. 3 shows the hydrophobicity plots (MACDNASIS PRO software) for TMP-1 (SEQ ID NO:1) and human CD53 (SEQ ID NO:3), respectively. The positive X axis reflects amino acid position, and the negative Y axis, hydrophobicity.

FIG. 4 shows the northern analysis for SEQ ID NO: 1. The northern analysis was produced electronically using LIFESEQFL database (Incyte Pharmaceuticals, Inc., Palo Alto, Calif.).

DESCRIPTION OF THE INVENTION

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence", as used herein, refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

A "composition comprising a given polynucleotide sequence", as used herein, refers broadly to any composition containing the given polynucleotide sequence. The composition may comprise an aqueous solution. Compositions comprising polynucleotide sequences encoding TMP-1 (SEQ ID NO:1) or fragments thereof (e.g., SEQ ID NO:2 and fragments thereof) may be employed as hybridization probes. In this case, the TMP-1-encoding polynucleotide sequences are typically employed in an aqueous solution containing salts (e.g., NaCI), detergents (e.g., SDS) and other components (e.g., Denhardt's solution, dry milk, salmon sperm DNA, etc.).

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

TMP-1, as used herein, refers to the amino acid sequences of substantially purified TMP-1 obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR (Perkin Elmer, Norwalk, Conn.) in the 5' and/or the 3' direction and resequenced, or which has been assembled from the overlapping sequences of more than one Incyte clone using the GELVIEW fragment assembly system (GCG, Madison, Wis.), or which has been both extended and assembled.

A "variant" of TMP-1, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic TMP-1, or any oligopeptide thereof, to induce a specific immune response in appropriate animals or cells and to bind with specific antibodies.

The term "agonist", as used herein, refers to a molecule which, when bound to TMP-1, causes a change in TMP-1 which modulates the activity of TMP-1. Agonists may include proteins, nucleic acids, carbohydrates, or any other molecules which bind to TMP-1.

The terms "antagonist" or "inhibitor", as used herein, refer to a molecule which, when bound to TMP-1, blocks or modulates the biological or immunological activity of TMP-1. Antagonists and inhibitors may include proteins, nucleic acids, carbohydrates, or any other molecules which bind to TMP-1.

The term "modulate", as used herein, refers to a change or an alteration in the biological activity of TMP-1. Modulation may be an increase or a decrease in protein activity, a change in binding characteristics, or any other change in the biological, functional, or immunological properties of TMP-1.

The term "mimetic", as used herein, refers to a molecule, the structure of which is developed from knowledge of the structure of TMP-1 or portions thereof and, as such, is able to effect some or all of the actions of TMP-1-like molecules.

The term "derivative", as used herein, refers to the chemical modification of a nucleic acid encoding TMP-1 or the encoded TMP-1. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences. Under "stringent conditions" SEQ ID NO:2 or fragments thereof will hybridize to its exact complement and closely related sequences. The stringent conditions are chosen such that SEQ ID NO:2 or fragments thereof will hybridize to sequences encoding human TMP-1 but not to sequences encoding human CD53 (i.e., SEQ ID NO:4 or its RNA equivalents). When fragments of SEQ ID NO:2 are employed in hybridization reactions, the stringent conditions include the choice of fragments of SEQ ID NO:2 to be used. Fragments of SEQ ID NO:2 which contain unique sequences (i.e., regions which are either non-homologous to or which contain less than about 50% homology or complementarity with SEQ ID NO:4) are preferentially employed. SEQ ID NO:4 represents DNA sequences encoding the human CD53 protein; this DNA sequence can be found in GenBank/NCBI as accession 180140.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human TMP-1 and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding TMP-1 or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding TMP-1 in a sample and thereby correlates with expression of the transcript from the polynucleotide encoding the protein.

"Alterations" in the polynucleotide of SEQ ID NO:2, as used herein, comprise any alteration in the sequence of polynucleotides encoding TMP-1 including deletions, insertions, and point mutations that may be detected using hybridization assays. Included within this definition is the detection of alterations to the genomic DNA sequence which encodes TMP-1 (e.g., by alterations in the pattern of restriction fragment length polymorphisms capable of hybridizing to SEQ ID NO:2), the inability of a selected fragment of SEQ ID NO:2 to hybridize to a sample of genomic DNA (e.g., using allele-specific oligonucleotide probes), and improper or unexpected hybridization, such as hybridization to a locus other than the normal chromosomal locus for the polynucleotide sequence encoding TMP-1 (e.g., using fluorescent in situ hybridization [FISH] to metaphase chromosomes spreads).

As used herein, the term "antibody" refers to intact molecules as well as fragments thereof, such as Fab, F(ab')$_2$, and Fv, which are capable of binding the epitopic determinant. Antibodies that bind TMP-1 polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of a novel human integral membrane protein (TMP-1) which is a member of the TM4SF superfamily, the polynucleotides encoding TMP-1, and the use of these compositions for the diagnosis, prevention, or treatment of diseases associated with abnormal expression of TMP-1. In addition, as mRNA encoding TMP-1 is found in a number of tumors, TMP-1 serves as a marker for cancerous cells, particularly brain, breast and prostate tumor cells.

Nucleic acids encoding the human TMP-1 of the present invention were first identified in Incyte Clone 663665 from the SCORNOT01 cDNA library through a computer-generated search for amino acid sequence alignments. A consensus sequence, SEQ ID NO:2, was derived from the following overlapping and/or extended nucleic acid sequences: Incyte Clones 663655 (SCORNOT01), 675727 (CRBLNOT01), 777339 (COLNNOT05), 1444469 (THYRNOT03), and 1635613 and 1636686 (UTRSNOT06).

In one embodiment, the invention encompasses a polypeptide comprising the amino acid sequence of SEQ ID NO:1, as shown in FIGS. 1A and 1B. TMP-1 is 265 amino acids in length and contains four major hydrophobic segments, three of which are located in close proximity to the amino-terminus, characteristics in common with members of the TM4SF. These hydrophobic segments or transmembrane domains (TM1–4) are located at residues 10–34, 56–76, 81–106 and 229–258 of SEQ ID NO:1. TMP-1 lacks a typical secretory signal which suggests that the amino-terminus of TMP-1, like that of other TM4SF members, is intracytoplasmic. TMP-1 contains several of the consensus motifs suggested for TM4SF members [Wright, M. D. and Tomlinson, M. G. (1994) Immunol. Today 15:588 and Robinstein, E. et al. (1993) Genomics 16:132]. The CCG and PXSC motifs located in the large extracellular domain of TM4SF proteins are found at residues 174–176 and 193–196 in the large extracellular domain of SEQ ID NO:1 and an imperfect match to the EGC consensus is located at residues 202–204 within the large extracellular domain of SEQ ID NO:1. In addition, TMP-1 contains the highly conserved asparagine in TM1 (i.e., $N_{17}$) and glutamic acid or glutamine residues in TM3 and TM4 (i.e., $E_{97}$ and $Q_{243}$, respectively). In addition, TMP-1 contains a sequence which has been identified as a TM4SF signature sequence in the PROSITE Dictionary of Protein Sites and Patterns at residues 68–83 of SEQ ID NO:1.

TMP-1 contains thirteen cysteine residues (i.e., $C_5$, $C_{25}$, $C_{72}$) $C_{81}$, $C_{174}$, $C_{175}$, $C_{196}$, $C_{197}$, $C_{204}$, $C_{217}$, $C_{238}$, $C_{255}$ and $C_{264}$). In addition to providing sites for disulfide bond formation, the cysteine residues provide potential sites for palmitoylation. Nine of the thirteen cysteine residues found in human TMP-1 are conserved in location with cysteine residues found in the human CD53 protein (i.e., $C_{25}$, $C_{72}$, $C_{81}$, $C_{174}$, $C_{175}$, $C_{197}$, $C_{204}$, $C_{238}$, and $C_{255}$ of TMP-1; see FIG. 2). The human TMP-1 of the present invention contains numerous potential O-linked glycosylation sites (i.e., serine and threonine residues). TMP-1 has two potential N-linked glycoslyation sites (i.e., Asn-Xaa-Ser/Thr) (i.e., $N_{179}$ and $N_{188}$) which are both located in the second or large extracellular domain (i.e., residues 107–228). In addition, the human TMP-1 of the present invention contains numerous potential phosphorylation sites (i.e., typically the hydroxyl groups of serine, threonine and tyrosine residues although asparagine, histidine and lysine residues may also be phosphorylated). In particular, TMP-1 has three potential protein kinase C phosphorylation sites (Ser/Thr-Xaa-Arg/Lys) located at residues 108–110, 163–165 and 220–222. TMP-1 contains seven potential N-myristoylation sites (i.e., residues 31–36, 39–44, 71–76, 127–132, 133–138, 236–241 and 246–251); these sites are located internally to TMP-1 and therefore proteolytic processing which exposes an internal glycine would be a prerequisite to N-myristoylation of TMP-1.

The TMP-1 protein of the present invention, like the human CD53 protein, has a slightly basic isoelectric point (pI) (TMP-1 has a pI of 7.26 and CD53 has a pI of 7.34). As illustrated by FIGS. 3A and 3B, the TMP-1 and human CD53 proteins have similar hydrophobicity plots which reveal four hydrophobic or transmembrane (TM) domains and two extracellular domains, the smaller extracellular domain located between TM1 and TM2 and the larger extracellular domain located between TM3 and TM4.

TMP-1 has chemical and structural homology with the human CD53 protein (GI 180141; SEQ ID NO:3) (Amiot, M., supra). Consistent with the pattern seen among TM4SF members, TMP-1 and human CD53 share a higher degree of homology in the transmembrane domains than in the extracellular domains, with the second and larger extracellular domain, showing the least degree of conservation. In particular, TMP-1 and human CD53 share 57% identity and 75% similarity over TM1 (residues 9–36 of TMP-1 and CD53), 38% identity and 76% similarity over TM2 (residues 56–76 of TMP-1 and residues 55–75 of CD53), 58% identity and 81% similarity over TM3 (residues 82–107 of TMP-1 and residues 81–106) and 37% identity and 74% similarity over TM4 (residues 229–256 of TMP-1 and residues 182–208 of CD53). A pair of residues are said to be similar if they represent conservative substitutions. FIG. 2 provides an alignment between the amino acid sequences of SEQ ID NOs: 1 and 3.

TMP-1 shares chemical and structural homology with a number of other TM4SF proteins including, but not limited to, the mouse and rat CD53 proteins, human, rabbit and mouse CD63/ME491 proteins, human and mouse CD37, human CD81/TAPA-1 proteins, human PETA-3 protein and human, cat and cow CD9/MRP-1. As discussed above, a number of these TM4SF members are associated with the regulation of cell growth and activation and/or cell motility and metastatic potential.

Northern analysis (FIG. 4) shows the expression of TMP-1-encoding sequences in various libraries, at least 35% of which are cancerous or immortalized (including the teratocarcinoma cell line hNT2) and at least 5% of which are involved with the immune response, including inflammatory and/or autoimmune disease (e.g., rheumatoid synovium, ulcerative colitis, asthmatic lung). Of particular note is the expression of TMP-1 mRNA in brain tumor (4/56), breast tumor (3/56), and prostate tumor (3/56) libraries. This pattern of expression demonstrates that TMP-1 serves as a marker for cancerous cells, particularly brain, breast and prostate tumor cells.

Of particular interest is the pattern of TMP-1 expression among apparently normal and tumorous lung tissue. Higher levels of TMP-1 are observed in apparently normal adult lung tissue (range of percent abundance: 0.03–0.08; mean: 0.4; values taken from FIG. 4 and rounded) than in a metastatic lung tumor (0.02 percent abundance). In addition, the abundance of TMP-1 is lower in metastatic brain tumor (0.0075) than in brain tumors (mean: 0.03). This pattern of expression suggests that a decrease in TMP-1 relative to normal or tumorous, but not metastatic, tissue may indicate the development or an increase in metastatic potential. In this regard, TMP-1 expression is reminiscent of the expression of CD63 which is a marker for early stages of melanoma progression; CD63 expression decreases as melanomas enter advanced (e.g., metastatic) stages. CD63 is also strongly expressed in prostate and colon carcinomas. It is noted that TMP-1 is expressed in several prostate tumor cell libraries. The expression of another TM4SF member, CD9, has been shown to correlate with the inhibition of metastatic potential.

The invention also encompasses TMP-1 variants. A preferred TMP-1 variant is one having at least 80%, and more preferably 90%, amino acid sequence similarity to the TMP-1 amino acid sequence (SEQ ID NO:1). A most preferred TMP-1 variant is one having at least 95% amino acid sequence similarity to SEQ ID NO: 1.

The invention also encompasses polynucleotides which encode TMP-1. Accordingly, any nucleic acid sequence which encodes the amino acid sequence of TMP-1 can be used to generate recombinant molecules which express TMP-1. In a particular embodiment, the invention encompasses the polynucleotide comprising the nucleic acid sequence of SEQ ID NO:2 as shown in FIGS. 1A and 1B.

It will be appreciated by those skilled in the art that as a result of the degeneracy of the genetic code, a multitude of nucleotide sequences encoding TMP-1, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring TMP-1, and all such variations are to be considered as being specifically disclosed.

Although nucleotide sequences which encode TMP-1 and its variants are preferably capable of hybridizing to the nucleotide sequence of the naturally occurring TMP-1 under appropriately selected conditions of stringency, it may be advantageous to produce nucleotide sequences encoding TMP-1 or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding TMP-1 and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode TMP-1 and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding TMP-1 or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding TMP-1 which are encompassed by the invention include deletions, insertions, or substitutions of different nucleotides resulting in a polynucleotide that encodes the same or a functionally equivalent TMP-1. The encoded protein may also contain deletions, insertions, or substitutions of amino acid residues which produce a silent change and result in a functionally equivalent TMP-1. Deliberate amino acid substitutions may be made on the basis of similarity in polarity, charge, solubility, hydrophobicity, hydrophilicity, and/or the amphipathic nature of the residues as long as the biological activity of TMP-1 is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding TMP-1. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill), or combinations of recombinant polymerases and proofreading exonucleases such as the ELONGASE amplification system marketed by Gibco BRL (Gaithersburg, Md.). Preferably, the process is automated with machines such as the Hamilton MICROLAB 2200 (Hamilton, Reno, Nev.), Peltier thermal cycler (PTC200; MJ Research, Watertown, Mass.) and the ABI 377 DNA sequencers (Perkin Elmer).

The nucleic acid sequences encoding TMP-1 may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°-72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode TMP-1, or fusion proteins or functional equivalents thereof, may be used in recombinant DNA molecules to direct expression of TMP-1 in appropriate host cells. Due to the inherent degeneracy of the genetic code, other DNA sequences which encode substantially the same or a functionally equivalent amino acid sequence may be produced and these sequences may be used to clone and express TMP-1.

As will be understood by those of skill in the art, it may be advantageous to produce TMP-1-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter TMP-1 encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding TMP-1 may be ligated to a heterologous sequence to encode a fusion protein. For example, to screen peptide libraries for inhibitors of TMP-1 activity, it may be useful to encode a chimeric TMP-1 protein that can be recognized by a commercially available antibody. A fusion protein may also be engineered to contain a cleavage site located between the TMP-1 encoding sequence and the heterologous protein sequence, so that TMP-1 may be cleaved and purified away from the heterologous moiety.

In another embodiment, sequences encoding TMP-1 may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of TMP-1, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) Proteins, Structures and Molecular Principles, W. H. Freeman and Co., New York, N.Y.). The composition of the synthetic peptides may be confirmed by amino acid analysis or sequencing (e.g., the Edman degradation procedure; Creighton, supra). Additionally, the amino acid sequence of TMP-1, or any part thereof, may be altered during direct synthesis and/or combined using chemical methods with sequences from other proteins, or any part thereof, to produce a variant polypeptide.

In order to express a biologically active TMP-1, the nucleotide sequences encoding TMP-1 or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding TMP-1 and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A variety of expression vector/host systems may be utilized to contain and express sequences encoding TMP-1. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector-enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding TMP-1, vectors based on SV40 or EBV may be used with an appropriate selectable marker.

In bacterial systems, a number of expression vectors may be selected depending upon the use intended for TMP-1. For example, when large quantities of TMP-1 are needed for the induction of antibodies, vectors which direct high level expression of fusion proteins that are readily purified may be used. Such vectors include, but are not limited to, the multifunctional E. coli cloning and expression vectors such as BLUESCRIPT (Stratagene), in which the sequence encoding TMP-1 may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomvces cerevisiae, a number of vectors containing constitutive or inducible promoters such as alpha factor, alcohol oxidase, and PGH may be used. For reviews, see Ausubel et al. (supra) and Grant et al. (1987) Methods Enzymol. 153:516–544. In cases where plant expression vectors are used, the expression of sequences encoding TMP-1 may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express TMP-1. For example, in one such system, Autographa californica nuclear polyhedrosis virus (AcNPV) is used as a vector to express foreign genes in Spodoptera frugiperda cells or in Trichoplusia larvae. The sequences encoding TMP-1 may be cloned into a non-essential region of the virus, such as the polyhedrin gene, and placed under control of the polyhedrin promoter. Successful insertion of TMP-1 will render the polyhedrin gene inactive and produce recombinant virus lacking coat protein. The recombinant viruses may then be used to infect, for example, S. frugiperda cells or Trichoplusia larvae in which TMP-1 may be expressed (Engelhard, E. K. et al. (1994) Proc. Natl. Acad. Sci. 91:3224–3227).

In mammalian host cells, a number of viral-based expression systems may be utilized. In cases where an adenovirus is used as an expression vector, sequences encoding TMP-1 may be ligated into an adenovirus transcription/translation complex consisting of the late promoter and tripartite leader sequence. Insertion in a non-essential E1 or E3 region of the viral genome may be used to obtain a viable virus which is capable of expressing TMP-1 in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding TMP-1. Such signals include the ATG initiation codon and adjacent sequences. In cases where sequences encoding TMP-1, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO (ATCC CCL 61 and CRL 9618), HeLa (ATCC CCL 2), MDCK (ATCC CCL 34 and CRL 6253), HEK 293 (ATCC CRL 1573), WI-38 (ATCC CCL 75) (ATCC: American Type Culture Collection, Rockville, Md.), which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express TMP-1 may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^-$ or $aprt^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, βglucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding TMP-1 is inserted within a marker gene sequence, recombinant cells containing sequences encoding TMP-1 can be identified by the absence of marker gene function. Alternatively, a marker gene can be placed in tandem with a sequence encoding TMP-1 under the control of a single promoter. Expression of the marker gene in response to induction or selection usually indicates expression of the tandem gene as well.

Alternatively, host cells which contain the nucleic acid sequence encoding TMP-1 and express TMP-1 may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding TMP-1 can be detected by DNA-DNA or DNA-RNA hybridization or amplification using probes or portions or fragments of polynucleotides encoding TMP-1. Nucleic acid amplification based assays involve the use of oligonucleotides or oligomers based on the sequences encoding TMP-1 to detect transformants containing DNA or RNA encoding TMP-1. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of TMP-1, using either polyclonal or monoclonal antibodies specific for the protein are known in the art. Examples include enzyme-linked immunosorbant assay (ELISA), radioimmunoassay (RIA), and fluorescence activated cell sorting (FACS). A two-site, monoclonal-based immunoassay utilizing monoclonal antibodies reactive to two non-interfering epitopes on TMP-1 is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding TMP-1 include oligolabeling, nick translation, end-labeling or PCR amplification using a labeled nucleotide. Alternatively, the sequences encoding TMP-1, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding TMP-1 may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode TMP-1 may be designed to contain signal sequences which direct secretion of TMP-1 through a prokaryotic or eukaryotic cell membrane. When it is desired to express a secreted form of TMP-1, a polynucleotide sequence encoding the extracellular domain(s) (i.e., residues 35–55 and 107–228 of SEQ ID NO:1) is preferentially employed. The two extracellular domains may be joined by TMP-1 or non-TMP-1 sequences if it is desired that a single polypeptide comprises both extracellular domains of TMP-1 be expressed. Alternatively, TMP-1 may be expressed as a membrane-bound protein in a host cell and the recombinant TMP-1 recovered from the membrane of the host cell using techniques well known to the art.

Other recombinant constructions may be used to join sequences encoding TMP-1 to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and TMP-1 may be used to facilitate purification. One such expression vector provides for expression of a fusion protein containing TMP-1 and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3: 263–281) while the enterokinase cleavage site provides a means for purifying TMP-1 from the fusion protein. A discussion of vectors which contain fusion proteins is provided in Kroll, D. J. et al. (1993; DNA Cell Biol. 12:441–453).

In addition to recombinant production, fragments of TMP-1 may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A peptide synthesizer (Perkin Elmer). Various fragments of TMP-1 may be chemically synthesized separately and combined using chemical methods to produce the full length molecule.

THERAPEUTICS

Based on the chemical and structural homology among TMP-1 (SEQ ID NO:1) and the human CD53 protein (SEQ ID NO:3) and other proteins in the TM4SF, TMP-1 appears to be a new member of the TM4SF. CD53 has been shown to be involved in the regulation of cell growth and activation and to be coupled to a variety of signal transduction pathways. Based on the homology between TMP-1 and CD53, as well as the homology between TMP-1 and other members of the TM4SF, it is believed that TMP-1 plays a role in the regulation of cell growth and activation. Improper regulation of cell growth is observed in tumors and thus, the amino acid and nucleic acid sequences of TMP-1 provided herein provide a means of producing therapeutic compounds for the treatment of disease states associated with altered TMP-1 expression.

As shown herein (FIG. 4), TMP-1 is expressed in apparently normal adult lung tissue as well as in a metastatic lung tumor. Since abundance of TMP-1 is lower in metastatic brain tumor than in other brain tumors, its pattern of expression suggests that a decrease in TMP-1 relative to normal or tumorous, but not metastatic, tissue may indicate the development of or an increase in metastatic potential. In addition, TMP-1 is expressed in a variety of other tumor types including prostate, breast, bladder, testicular, thyroid, skull, kidney and gall bladder.

Therefore, in one embodiment, TMP-1 or a fragment or derivative thereof may be administered to a subject to treat disorders associated with metastasis as well as a variety of tumors. Such conditions and diseases may include, but are not limited to, metastatic lung and brain tumors, and prostate, breast, bladder, testicular, thyroid, skull, kidney and gall bladder tumors.

In another embodiment, a vector capable of expressing TMP-1, or a fragment or a derivative thereof, may also be administered to a subject to treat the metastatic lung and brain tumors, and prostate, breast, bladder, testicular, thyroid, skull, kidney and gall bladder tumors described above.

In another embodiment, TMP-1 may be administered in combination with other conventional chemotherapeutic agents. The combination of therapeutic agents having different mechanisms of action will have synergistic effects allowing for the use of lower effective doses of each agent and lessening side effects.

In one aspect, agonists of TMP-1 may be used to increase the activity of TMP-1 in cells having reduced TMP-1 levels. Antibodies which are specific for TMP-1 may be used directly as an agonist, or indirectly as a targeting or delivery mechanism for bringing a pharmaceutical agent to cells or tissue which express TMP-1.

In one embodiment, antagonists or inhibitors of TMP-1 may be administered to a subject to treat or prevent tumors, particularly prostate, breast, bladder, testicular, thyroid, skull, kidney and gall bladder tumors.

In another embodiment, a vector expressing antisense of the polynucleotide encoding TMP-1 may be administered to a subject to treat or prevent tumors, particularly prostate, breast, bladder, testicular, thyroid, skull, kidney and gall bladder tumors.

Antagonists or inhibitors of TMP-1 may be produced using methods which are generally known in the art. In particular, purified TMP-1 may be used to produce antibodies or to screen libraries of pharmaceutical agents to identify those which specifically bind TMP-1.

Antibodies which are specific for TMP-1 may be used directly as an antagonist, or indirectly as a targeting or delivery mechanism for bringing a pharmaceutical agent to cells or tissue which express TMP-1. The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which reduce or abolish TMP-1 activity) are especially preferred for therapeutic use.

For the production of antibodies, various hosts including goats, rabbits, rats, mice, humans, and others, may be immunized by injection with TMP-1 or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to TMP-1 have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of TMP-1 amino acids may be fused with those of another protein such as keyhole limpet hemocyanin and antibody produced against the chimeric molecule.

Monoclonal antibodies to TMP-1 may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce TMP-1-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for TMP-1 may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between TMP-1 and its specific antibody. A two-site, monoclonal-based immunoassay utilizing monoclonal antibodies reactive to two non-interfering TMP-1 epitopes is preferred, but a competitive binding assay may also be employed (Maddox, supra).

In another embodiment of the invention, the polynucleotides encoding TMP-1, or any fragment thereof, or antisense molecules, may be used for therapeutic purposes. In one aspect, antisense to the polynucleotide encoding TMP-1 may be used in situations in which it would be desirable to block the transcription of the mRNA. In particular, cells may be transformed with sequences complementary to polynucleotides encoding TMP-1. Thus, antisense molecules may be used to modulate TMP-1 activity, or to achieve regulation of gene function. Such technology is now well known in the art, and sense or antisense oligomers or larger fragments, can be designed from various locations along the coding or control regions of sequences encoding TMP-1.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding TMP-1. These techniques are described both in Sambrook et al. (supra) and in Ausubel et al. (supra).

Genes encoding TMP-1 can be turned off by transforming a cell or tissue with expression vectors which express high levels of a polynucleotide or fragment thereof which encodes TMP-1. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding TMP-1, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.)., The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding TMP-1.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding TMP-1. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of TMP-1, antibodies to TMP-1, mimetics, agonists, antagonists, or inhibitors of TMP-1. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of TMP-1, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example TMP-1 or fragments thereof, antibodies of TMP-1, agonists, antagonists or inhibitors of TMP-1, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it can be expressed as the ratio LD50/ED50.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind TMP-1 may be used for the diagnosis of conditions or diseases characterized by expression of TMP-1, or in assays to monitor patients being treated with TMP-1, agonists, antagonists or inhibitors. The antibodies useful for diagnostic purposes may be prepared in the same manner as those described above for therapeutics. Diagnostic assays for TMP-1 include methods which utilize the antibody and a label to detect TMP-1 in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring TMP-1 are known in the art and provide a basis for diagnosing altered or abnormal levels of TMP-1 expression. Normal or standard values for TMP-1 expression are established by combining body fluids or cell extracts taken from normal mammalian subjects, preferably human, with antibody to TMP-1 under conditions suitable for complex formation. The amount of standard complex formation may be quantified by various methods, preferably by photometric means. Quantities of TMP-1 expressed in subject samples from biopsied tissues are compared with the standard values. Deviation between standard and subject values establishes the parameters for diagnosing disease.

In another embodiment of the invention, the polynucleotides encoding TMP-1 is used for diagnostic purposes. The polynucleotides which may be used include oligonucleotide sequences, antisense RNA and DNA molecules, and PNAs. The polynucleotides may be used to detect and quantitate gene expression in biopsied tissues in which expression of TMP-1 may be correlated with disease. The diagnostic assay may be used to distinguish between absence, presence, and excess expression of TMP-1, and to monitor regulation of TMP-1 levels during therapeutic intervention.

In one aspect, hybridization with PCR probes which are capable of detecting polynucleotide sequences, including genomic sequences, encoding TMP-1 or closely related molecules, may be used to identify nucleic acid sequences which encode TMP-1. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding TMP-1, alleles, or related sequences.

Probes may also be used for the detection of related sequences, and should preferably contain at least 50% of the nucleotides from any of the TMP-1 encoding sequences. The hybridization probes of the subject invention may be DNA or RNA and derived from the nucleotide sequence of SEQ ID NO:2 or from genomic sequence including promoter, enhancer elements, and introns of the naturally occurring TMP-1.

Means for producing specific hybridization probes for DNAs encoding TMP-1 include the cloning of nucleic acid sequences encoding TMP-1 or TMP-1 derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding TMP-1 may be used for the diagnosis of conditions or diseases which are associated with expression of TMP-1. Examples of such conditions or diseases include metastatic lung and brain tumors, and prostate, breast, bladder, testicular, thyroid, skull, kidney and gall bladder tumors. The polynucleotide sequences encoding TMP-1 may be used in Southern or northern analysis, dot blot, or other membrane-based technologies; in PCR technologies; or in dip stick, pin, ELISA or chip assays utilizing fluids or tissues from patient biopsies to detect altered TMP-1 expression. Such qualitative or quantitative methods are well known in the art.

In a particular aspect, the nucleotide sequences encoding TMP-1 provide the basis for assays that detect activation or induction of various cancers, particularly those mentioned above; in addition the lack of expression of TMP-1 may be detected using the TMP-1-encoding nucleotide sequences disclosed herein. The nucleotide sequences encoding TMP-1 may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding TMP-1 in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of TMP-1, a normal or standard profile for expression is established. This may be accomplished by combining body fluids or cell extracts taken from normal subjects, either animal or human, with a sequence, or a fragment thereof, which encodes TMP-1, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively low or a relatively high amount of transcript in biopsied tissue from an individual may indicate a predisposition for the development of the disease or metastasis, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding TMP-1 may involve the use of PCR. Such oligomers may be chemically synthesized, generated enzymatically, or produced from a recombinant source. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of TMP-1 include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode TMP-1 may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding TMP-1 on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, TMP-1, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between TMP-1 and the agent being tested, may be measured.

Another technique for drug screening which may be used provides for high throughput screening of compounds having suitable binding affinity to the protein of interest as described in published PCT application WO84/03564. In this method, as applied to TMP-1 large numbers of different small test compounds are synthesized on a solid substrate, such as plastic pins or some other surface. The test compounds are reacted with TMP-1, or fragments thereof, and washed. Bound TMP-1 is then detected by methods well known in the art. Purified TMP-1 can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding TMP-1 specifically compete with a test compound for binding TMP-1. In this manner, the antibodies can be used to detect the presence of any peptide which shares one or more antigenic determinants with TMP-1.

In additional embodiments, the nucleotide sequences which encode TMP-1 may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I SCORNOT01 cDNA Library

The spinal cord cDNA library was constructed from tissue removed from a 71 year old, Caucasian male (lot #RA95-04-0255) and obtained from the Keystone Skin Bank (International Institute for Advanced Medicine, Exton Pa.). The tissue was flash frozen, ground in a mortar and pestle, and lysed immediately in a buffer containing guanidinium isothiocyanate. The lysate was extracted once with acid phenol, pH 4.0, once with phenol chloroform, pH 8.0, and then centrifuged over a CsCl cushion using a Beckman SW28 rotor in a L8-70M ultracentrifuge (Beckman Instruments). The RNA was precipitated using 0.3M sodium acetate and 2.5 volumes of ethanol, resuspended in water, and DNase treated for 15 min at 37° C. The poly $A^+$ RNA was isolated using OLIGOTEX kit (QIAGEN Inc. Chatsworth Calif.) and used to construct the cDNA library.

The RNA was handled according to the recommended protocols in the SUPERSCRIPT plasmid system for cDNA synthesis and plasmid cloning (catalog #18248-013; Gibco/BRL, Gaithersburg, Md.). cDNAs were fractionated on a SEPHAROSE CL4B column (catalog #275105, Pharmacia), and those cDNAs exceeding 400 bp were ligated into PSPORT 2. The plasmid PSPORT 1 was subsequently transformed into DH5α competent cells (Cat. #18258-012, Gibco/BRL).

II Isolation and Sequencing of cDNA Clones

Plasmid DNA was purified using the Miniprep Kit (Catalogue #77468, Advanced Genetic Technologies Corporation, Gaithersburg Md.), a 96-well block kit with reagents for 960 purifications. The recommended protocol included with the kit was employed except for the following changes. Each of the 96 wells was filled with only I ml of sterile Terrific Broth (Catalog #22711, LIFE TECHNOLOGIES) with carbenicillin at 25 mg/L and glycerol at 0.4%. After the wells were inoculated, the bacteria were cultured for 24 hours and lysed with 60 μl of lysis buffer. A centrifugation step (Beckman GS-6R@2900 rpm for 5 min; Beckman Instruments) was performed before the contents of the block were added to the primary filter plate. The optional step of adding isopropanol to TRIS buffer was not routinely performed. After the last step in the protocol, samples were transferred to a Beckman 96-well block for storage.

The cDNAs were sequenced by the method of Sanger F and AR Coulson (1975; J Mol Biol 94:441f), using a Hamilton MICROLAB 2200 (Hamilton, Reno Nev.) in combination with four Peltier thermal cyclers (PTC200 from MJ Research, Watertown Mass.) and Applied Biosystems 377 or 373 DNA sequencing systems (Perkin Elmer), and the reading frame was determined.

III Homology Searching of cDNA Clones and Their Deduced Proteins

Each cDNA was compared to sequences in GenBank using a search algorithm developed by Applied Biosystems and incorporated into the INHERIT 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT 670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

A comparison of the full-length and partial cDNA sequences and the deduced amino acid sequences corresponding to the human TMP-1 gene and TMP-1 protein with known nucleotide and protein sequences in GenBank revealed that the full-length human TMP-1 cDNA and protein sequences (i.e., SEQ ID NOS:1 and 2) were unique (i.e., not previously identified). This search revealed that the human TMP-1 protein shared some homology with the human CD53 protein (SEQ ID NO:3) and other members of the TM4SF including, but not limited to, the mouse and rat CD53 proteins (GenBank/NCBI Accession Nos: 1279546 and 205898, respectively), human, rabbit and mouse CD63/ME491 proteins (GenBank/NCBI: 189384, 684974 and 976238, respectively), human and mouse CD37 (GenBank/NCBI: 29794 and 755242, respectively), human CD81/TAPA-1 proteins (GenBank/NCBI: 180140), human PETA-3 protein (GenBank/NCBI: 541613) and human, cat and cow CD9/MRP-1 (GenBank/NCBI: g300115, 529228 and 162821, respectively). In addition, portions of the amino acid sequence of TMP-1 were found to share homology with a number of short EST sequences of human origin (e.g., GenBank/NCBI: 1357879, 1155756, 831070, 1163961, and 1137929).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding TMP-1 occurs. Abundance and percent abundance are also reported. Abundance directly reflects the number of times a particular transcript is represented in a cDNA library, and percent abundance is abundance divided by the total number of sequences examined in the cDNA library.

Electronic northern analysis (FIG. 4) revealed that mRNA encoding human TMP-1 (SEQ ID NO:1) was present in libraries generated from a wide variety of tissues. TMP-1 cDNA was most strongly expressed in the myometrium of the uterus and in adult lung. In addition to expression in apparently normal human tissues, TMP-1 was expressed in a variety of tumors, including but not limited to brain, prostate, breast and bladder tumors (including brain and lung metastasis) as well as in the immortalized hNT2 cell line which was derived from a teratocarcinoma. TMP-1 cDNA is also expressed in a variety of tissues and cell lines which are involved with the immune response, including inflammatory and/or autoimmune disease (e.g., rheumatoid synovium and ulcerative colitis).

V Extension of TMP-1-Encoding Polynucleotides

The nucleic acid sequence (SEQ ID NO:2) is used to design oligonucleotide primers for extending a nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 software (National Biosciences), or another appropriate program, to be 22–30 nucleotides in length, to have a GC content of 50% or more, and to anneal to the target sequence at temperatures about 68°–72° C Any stretch of nucleotides which would result in hairpin structures and primer-primer dimerization is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier thermal cycler (PTC200; M. J. Research, Watertown, Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 $\mu$l aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 $\mu$l of ligation buffer, 1$\mu$l T4-DNA ligase (15 units) and 1 $\mu$l T4 polynucleotide kinase are added, and the mixture is incubated at room temperature for 2–3 hours or overnight at 16° C. Competent E. coli cells (in 40 $\mu$l of appropriate media) are transformed with 3 $\mu$l of ligation mixture and cultured in 80 $\mu$l of SOC medium (Sambrook et al., supra). After incubation for one hour at 37° C, the whole transformation mixture is plated on Luria Bertani (LB)-agar (Sambrook et al., supra) containing 2x Carb. The following day, several colonies are randomly picked from each plate and cultured in 150 $\mu$l of liquid LB/2x Carb medium placed in an individual well of an appropriate, commercially-available, sterile 96-well microtiter plate. The following day, 5 $\mu$l of each overnight culture is transferred into a non-sterile 96-well plate and after dilution 1:10 with water, 5 $\mu$l of each sample is transferred into a PCR array.

For PCR amplification, 18 $\mu$l of concentrated PCR reaction mix (3.3x) containing 4 units of rTth DNA polymerase, a vector primer, and one or both of the gene specific primers used for the extension reaction are added to each well. Amplification is performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 software (National Biosciences), labeled by combining 50 pmol of each oligomer and 250 $\mu$Ci of [$\gamma$–$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, PstI, Xba 1, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR film (Kodak, Rochester, N.Y.) is exposed to the blots, or the blots are exposed to a Phosphoimager cassette (Molecular Dynamics, Sunnyvale, Calif.) hybridization patterns are compared visually.

VII Antisense Molecules

Antisense molecules to the TMP-1-encoding sequence, or any part thereof, is used to inhibit in vivo or in vitro expression of naturally occurring TMP-1. Although use of antisense oligonucleotides, comprising about 20 base-pairs, is specifically described, essentially the same procedure is used with larger cDNA fragments. An oligonucleotide based on the coding sequences of TMP-1, as shown in FIGS. 1A and 1B, is used to inhibit expression of naturally occurring TMP-1. The complementary oligonucleotide is designed from the most unique 5' sequence as shown in FIGS. 1A and 1B and used either to inhibit transcription by preventing promoter binding to the upstream nontranslated sequence or translation of an TMP-1-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIGS. 1A and 1B.

VIII Expression of TMP-1

Expression of TMP-1 is accomplished by subcloning the cDNAs into appropriate vectors and transforming the vectors into host cells. In this case, the cloning vector, pSport, previously used for the generation of the cDNA library is used to express TMP-1 in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein or fragments thereof. Sequences encoding the extracellular domains of TMP-1 fusion protein located at residues 35–55 and 107–228 of SEQ ID NO:1 are preferentially employed for the production of soluble forms of recombinant TMP-1. The two extracellular domains may be joined by TMP-1 or non-TMP-1 sequences if it is desired that a single polypeptide comprises both extracellular domains of TMP-1 be expressed. The signal residues present on the pSport vector direct the secretion of TMP-1 polypeptides into the bacterial growth media.

Alternatively, TMP-1 may be expressed as a membrane-bound protein in a host cell and the recombinant TMP-1 recovered from the membrane of the host cell using techniques well known to the art.

IX Demonstration of TMP-1 Activity

Given the chemical and structural similarity between the human TMP-1 and human CD53 proteins and other members of the TM4SF, TMP-1 is identified as a new member of the TM4SF and is presumed to be involved in the regulation of cell growth. In view of the expression pattern of TMP-1 (FIG. 4) which shows that TMP-1 levels are low in brain and lung metastases, expression of TMP-1 is presumed to be related to metastatic potential.

To demonstrate that low levels of TMP-1 expression correlates with an increase in metastatic potential or increased cell motility, expression vectors encoding TMP-1 are transfected (e.g., electroporated) into highly motile cell lines, such as U-937 (ATCC CRL 1593), HEL 92.1.7 (ATCC TIB 180) and MAC 10, and the motility of the transfected and untransfected (control) cells are compared. Methods for the design and construction of an expression vector capable of expressing TMP-1 in the desired mammalian cell line(s) chosen are well known to the art. Assays for examining the motility of cells in culture are known to the art [see, e.g., Miyake, M. et al. (1991) J. Exp. Med. 174:1347 and Ikeyama, S. et al. (1993), supra]. If increasing the level of TMP-1 in highly motile cell lines by transfection with a TMP-1 expression vector inhibits or reduces the motility of highly motile cell lines, then the level of TMP-1 expression correlates (inversely) with cell motility and/or metastatic potential.

In addition to the assay described above, the correlation between TMP-1 and metastatic potential can be measured using an animal model in which the invasiveness of a metastatic cell line [e.g., the mouse BL6 metastatic melanoma cell line; Hart, I. R. et al. (1979) Am. J. Pathol. 97:586 and Ikeyama, S. et al. (1993), supra] transfected with a TMP-1 expression vector is compared with the invasiveness of the untransfected metastatic cell line.

X Production of TMP-1 Specific Antibodies

TMP-1 that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc.) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431A peptide synthesizer using finoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring TMP-1 Using Specific Antibodies

Naturally occurring or recombinant TMP-1 is substantially purified by immunoaffinity chromatography using antibodies specific for TMP-I. An immunoaffinity column is constructed by covalently coupling TMP-1 antibody to an activated chromatographic resin, such as CnBr-activated SEPHAROSE (Pharmacia & Upjohn). After the coupling, the resin is blocked and washed according to the manufacturer's instructions.

Media containing TMP1 is passed over the immunoaffinity column, and the column is washed under conditions that allow the preferential absorbance of TMP-1 (e.g., high ionic strength buffers in the presence of detergent). The column is eluted under conditions that disrupt antibody/TMP-1 binding (e.g., a buffer of pH 2–3 or a high concentration of a chaotrope, such as urea or thiocyanate ion), and TMP-1 is collected.

XII Identification of Molecules Which Interact with TMP-1

TMP-1 or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled TMP-1, washed and any wells with labeled TMP-1 complex are assayed. Data obtained using different concentrations of TMP-1 are used to calculate values for the number, affinity, and association of TMP-1 with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding a polypeptide comprising the amino acid sequence of SEQ ID NO:1.

2. An expression vector containing the polynucleotide sequence of claim 1.

3. A host cell containing the expression vector of claim 2.

4. An isolated and purified polynucleotide sequence comprising SEQ ID NO:2.

5. An isolated and purified polynucleotide sequence which is complementary to the polynucleotide sequence of claim 4.

6. A method for detection of a polynucleotide encoding a polypeptide comprising the amino acid sequence of SEQ ID NO:1 in a biological sample containing nucleic acid material, the method comprising the steps of:

a) hybridizing the polynucleotide of claim 5 to the nucleic acid material of the biological sample, thereby forming a hybridization complex; and b) detecting the hybridization complex, wherein the presence of the hybridization complex correlates with the presence of the polynucleotide in the biological sample.

7. The method of claim 6, wherein the nucleic acid material of the biological sample is amplified by the polymerase chain reaction before the hybridizing step.

* * * * *